(12) United States Patent
Brelvi et al.

(10) Patent No.: US 9,737,603 B1
(45) Date of Patent: Aug. 22, 2017

(54) ALCOHOL-BASED LOCAL ANESTHESIA AND ASSOCIATED USE THEREOF

(71) Applicants: Zamir Brelvi, Montville, NJ (US); Kamal Dutta, Montville, NJ (US); Anila Baig, Montville, NJ (US)

(72) Inventors: Zamir Brelvi, Montville, NJ (US); Kamal Dutta, Montville, NJ (US); Anila Baig, Montville, NJ (US)

( * ) Notice: Subject to any disclaimer, the term of this patent is extended or adjusted under 35 U.S.C. 154(b) by 0 days.

(21) Appl. No.: 14/965,688

(22) Filed: Dec. 10, 2015

Related U.S. Application Data

(60) Provisional application No. 62/090,296, filed on Dec. 10, 2014.

(51) Int. Cl.
| | |
|---|---|
| *A01N 37/12* | (2006.01) |
| *A01N 37/44* | (2006.01) |
| *A61K 31/24* | (2006.01) |
| *A61K 47/10* | (2017.01) |
| *A61K 9/00* | (2006.01) |
| *A61K 31/245* | (2006.01) |
| *A61K 31/05* | (2006.01) |
| *A61K 9/06* | (2006.01) |

(52) U.S. Cl.
CPC ............ *A61K 47/10* (2013.01); *A61K 9/0014* (2013.01); *A61K 9/06* (2013.01); *A61K 31/05* (2013.01); *A61K 31/245* (2013.01)

(58) Field of Classification Search
None
See application file for complete search history.

(56) References Cited

FOREIGN PATENT DOCUMENTS

JP    WO/2007/111371    * 10/2007

OTHER PUBLICATIONS

Rosa, et. al., Anesthesia Progress (46) 1999, pp. 97-99.*

* cited by examiner

*Primary Examiner* — Jeffrey H Murray
(74) *Attorney, Agent, or Firm* — Ashkan Najafi

(57) ABSTRACT

An alcohol-based topical numbing agent can be applied to an epithelial surface via a cotton swab or other suitable applicator for providing an anesthetic and analgesic effect on skin tissue. The alcohol-based topical numbing agent includes a topical homogenous chemical composition including a primary solvent including a safe and effective quantity of isopropyl alcohol; a secondary solvent including a safe and effective quantity of water; at least one anesthetic including a safe and effective quantity of benzocaine; and a safe and effective quantity of a skin analgesic including menthol.

12 Claims, 5 Drawing Sheets

Liquid Form: Alcohol-based topical numbing agent (topical homogenous anesthesia chemical composition 10)

> a primary solvent including a safe and effective quantity of isopropyl alcohol; between 70% (v) to 75% (v) of said topical homogenous chemical composition > a secondary solvent including a safe and effective quantity of water; between 2% (v) and 24% (v) of said topical homogenous chemical composition > at least one anesthetic including a safe and effective quantity of benzocaine; between 5% (w/v) and 20% (w/v) of said topical homogenous chemical > a safe and effective quantity of a skin analgesic including menthol; between 1% (w/v) and 3% (w/v) of said topical homogenous chemical

Figure 1

Liquid Form: Alcohol-based topical numbing agent (topical homogenous anesthesia chemical composition 10)

safe and effective quantity of isopropyl alcohol is 74% (v) of said topical homogenous chemical composition, safe and effective quantity of benzocaine is 15% (w/v) of said homogenous chemical solution, safe and effective quantity of water is 10% (v) of said topical homogenous chemical composition, menthol is 1% (w/v) of said topical homogenous chemical composition.

Figure 2

Cream Form: Alcohol-based topical numbing agent (topical homogenous anesthesia chemical composition 10')

safe and effective quantity of isopropyl alcohol is between 5% (v) to 15% (v)

safe and effective quantity of benzocaine is between 2% (w/v) and 20% (w/v) of said topical homogenous chemical composition safe and effective quantity of water is between 64% (v) and 92.9% (v) of said topical homogenous chemical composition menthol is between 0.1% (w/v) and 1% (w/v) of said topical homogenous chemical composition

Figure 3

A method of utilizing an alcohol-based topical numbing agent for providing an anesthetic effect on skin tissue 11 obtaining a topical homogenous chemical composition including a primary solvent including a safe and effective quantity of isopropyl alcohol, a secondary solvent including a safe and effective quantity of water, at least one anesthetic including a safe and effective quantity of benzocaine, and a safe and effective quantity of a skin analgesic including menthol;

applying said topical homogenous chemical composition to an epithelial tissue of a user.

Figure 4

A method of preparing one liter of an alcohol-based topical numbing agent for providing an anesthetic effect on skin tissue 12

- obtaining and weighing 150 gms of benzocaine;
- obtaining and weighing 10 gms of menthol;
- adding said benzocaine and said menthol to a two liter flask;
- obtaining and weighing 567 gms (740 ml) of isopropyl alcohol;
- adding said isopropyl alcohol to said benzocaine and said menthol;
- obtaining and weighing 100 gms (100ml) of distilled water;
- adding said distilled water to said benzocaine, said menthol and said isopropyl alcohol
- sealing and shaking said flask at 200 revolutions per minute for 60 minutes at approximately 25C

Figure 5

ALCOHOL-BASED LOCAL ANESTHESIA AND ASSOCIATED USE THEREOF

CROSS REFERENCE TO RELATED APPLICATIONS

This is a non-provisional patent application that claims the benefit of U.S. provisional patent application No. 62/090,296 filed Dec. 10, 2014, which is incorporated by reference herein in its entirety.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF NON-LIMITING EXEMPLARY EMBODIMENT(S) OF THE PRESENT DISCLOSURE

Technical Field

Exemplary embodiment(s) of the present disclosure relate to topical skin numbing agents and, more particularly, to an alcohol-based (liquid) topical skin numbing agent that can be applied to an epithelial surface via a cotton swab or other suitable applicator.

Prior Art

About 26 million patients suffer from diabetes in the US, wherein about 10 million of such patients have to measure their blood glucose by performing a finger stick procedure every day. About 1 billion phlebotomy procedures are performed annually in the US. About 27,000 children are vaccinated daily in the US. Currently, before these procedures are performed, the patients' skin is cleaned with an antiseptic solution of 70% Isopropyl Alcohol. In some cases, the skin is anesthetized using a cream based preparation called Eutectic Mixture of Local Anesthetics (EMLA®).

Historically, dermal anesthesia for minor skin surgery has been achieved by the injection of anesthetic solution via a needle and syringe. Although this technique is effective, it suffers from several drawbacks. Many patients, especially children, do not tolerate the pain of an injection well. Also, injection of topical anesthetic into an allergic patient could result in a severe reaction.

The state of the art shows an increase in the use of topical anesthetic over injected anesthetics. Topical anesthetics act via a loss of sensation in the localized area of administration in the body. The mechanism by which topical anesthetics induce their effect, while not having been determined definitively, is generally thought to be based upon the ability to topically interfere with the initiation and transmission of a nerve impulse, e.g., interfering with the initiation and/or propagation of a depolarization wave in a localized area of nerve tissue.

In recent years, creams containing EMLA® such as lidocaine and prilocaine have been found useful as a topical anesthetic for superficial skin procedures. The EMLA® cream is applied to a lesion and adjacent tissue and covered with an occlusive dressing for about 20 minutes to about 2 hours.

While the EMLA® and topical lidocaine creams are welcome alternatives to anesthetic injection, they have several drawbacks. A major inconvenience is that local anesthesia of intact skin for minor procedures is not achieved until at least 60 minutes following application. For more invasive procedures, at least two hours may be required. This delay in onset is a significant disadvantage, as it is a great inconvenience for both patients and medical staff. Such delay is particularly a problem in the area of pediatrics, where any additional time spent awaiting treatment only contributes to the anxiety of the patient.

Another disadvantage with EMLA® cream is that, for deep penetrative effect, it is necessary that the cream be applied under an occlusive dressing. Specifically, a bilayer of laminate and absorbent cellulose is taped to the area of the skin to be anesthetized. Such a dressing is inconvenient and messy.

Furthermore, skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels to be so absorbed; molecules must overcome a different resistance to penetration in each type of tissue. Transport across the skin membrane is thus a complex phenomenon. However, it is the cells of the stratum corneum, which present the primary barrier to absorption of topical compositions or transdermally administered drugs.

This impermeability may be attributed to the nature of one very thin layer created by normal development and physiological changes in the skin. After cells are formed in the basal layer, they begin to migrate toward the skin surface, until they are eventually sloughed off. As they undergo this migration, they become progressively more dehydrated and keratinized. When they reach the surface, just prior to being discarded, they form a thin layer of dense, metabolically inactive cells approximately ten microns (10-15 cells) thick, the stratum corneum or "cornified layer." As a result of the high degree of keratinization of the cells, which comprise the stratum corneum, a formidable barrier is created. Absorption through a mucosal surface is generally efficient because the stratum corneum is absent. Therefore, any formulation to be utilized as an efficient topical, transdermal anesthetic must be capable of being readily absorbed through the skin.

In addition to the thickness and integrity of the stratum corneum epidermis, percutaneous or transdermal absorption can significantly alter drug kinetics and depend on a variety of factors including site of application, size of active drug molecule, permeability of the membrane of the transdermal drug delivery system, state of skin hydration, pH of the drug, drug metabolism by skin flora, lipid solubility, and alteration of blood flow in the skin by additives and body temperature.

To increase the rate of penetration of drugs across the skin, the prior art shows the use of various skin penetration enhancers. Currently available percutaneous and transmucosal penetration enhancers use solvents or detergents to alter the physical properties of the multilayered lipid bilayers. Such agents include dimethylsulfoxide (DMSO), oleyl alcohol (OA), propylene glycol (PG), methyl pyrrolidone and AZONE® (dodecylazyl cycloheptan 2-one). However, unfortunately, the uses of the known penetration enhancers are associated with disadvantages.

For one, the penetration enhancer is typically co-administered with the desired drug. That is, the penetration enhancer passes through the patient's skin at the same time the drug does. Depending upon the exact nature of the penetration enhancer, this can lead to side effects related directly to the penetration enhancers.

Another disadvantage is that the addition of penetration enhancers tends to change the concentration of the drug, which presents the problem of difficulties in achieving an acceptable delivery rate of the medicament that needs to be delivered through the skin.

Another disadvantage is that the enhancers are often organic solvents, which can, in some cases, react with and alter the character of the drug being delivered. In addition, the enhancers can interact with the patient's skin, in some cases causing irritation and the like.

Accordingly, a need remains for an alcohol-based (liquid) topical numbing agent in order to overcome at least one prior art shortcoming. In particular, there is a need for a simple chemical composition that would both be an antiseptic and an anesthetic. The exemplary embodiment(s) satisfy such a need by providing an alcohol-based (liquid) topical numbing agent that is convenient and easy to use, lightweight yet durable in design, versatile in its applications, and designed that can be applied to an epithelial surface via a cotton swab or other suitable applicator.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide an alcohol-based topical numbing agent for providing an anesthetic effect on skin tissue. These and other objects, features, and advantages of the non-limiting exemplary embodiment(s) are provided by the alcohol-based topical numbing agent including: a topical homogenous chemical composition including a primary solvent including a safe and effective quantity of isopropyl alcohol; a secondary solvent including a safe and effective quantity of water; at least one anesthetic including a safe and effective quantity of benzocaine; and a safe and effective quantity of a skin analgesic including menthol.

In a non-limiting exemplary embodiment, the topical homogenous chemical composition is a liquid.

In a non-limiting exemplary embodiment, the safe and effective quantity of isopropyl alcohol is between 70% (v) to 75% (v) of the topical homogenous chemical composition.

In a non-limiting exemplary embodiment, the safe and effective quantity of benzocaine is between 5% (w/v) and 20% (w/v) of the topical homogenous chemical composition.

In a non-limiting exemplary embodiment, the safe and effective quantity of water is between 2% (v) and 24% (v) of the topical homogenous chemical composition.

In a non-limiting exemplary embodiment, the menthol is between 1% (w/v) and 3% (w/v) of the topical homogenous chemical composition.

In a non-limiting exemplary embodiment, the safe and effective quantity of isopropyl alcohol is 74% (v) of the topical homogenous chemical composition, wherein the safe and effective quantity of benzocaine is 15% (w/v) of the homogenous chemical solution, wherein the safe and effective quantity of water is 10% (v) of the topical homogenous chemical composition, and wherein the menthol is 1% (w/v) of the topical homogenous chemical composition.

In a non-limiting exemplary embodiment, the topical homogenous chemical composition is a cream.

In a non-limiting exemplary embodiment, the safe and effective quantity of isopropyl alcohol is between 5% (v) to 15% (v).

In a non-limiting exemplary embodiment, the safe and effective quantity of benzocaine is between 2% (w/v) and 20% (w/v) of the topical homogenous chemical composition.

In a non-limiting exemplary embodiment, the safe and effective quantity of water is between 64% (v) and 92.9% (v) of the topical homogenous chemical composition.

In a non-limiting exemplary embodiment, the menthol is between 0.1% (w/v) and 1% (w/v) of the topical homogenous chemical composition.

The present disclosure further includes a method of utilizing an alcohol-based topical numbing agent for providing an anesthetic effect on skin tissue. Such a method including the steps of: obtaining a topical homogenous chemical composition including a primary solvent including a safe and effective quantity of isopropyl alcohol, a secondary solvent including a safe and effective quantity of water, at least one anesthetic including a safe and effective quantity of benzocaine, and a safe and effective quantity of a skin analgesic including menthol; and applying the topical homogenous chemical composition to an epithelial tissue of a user.

In a non-limiting exemplary embodiment, a method of preparing one liter of an alcohol-based topical numbing agent includes the steps of: obtaining and weighing 150 gms of benzocaine; obtaining and weighing 10 gms of menthol; adding the benzocaine and the menthol to a two liter flask; obtaining and weighing 567 gms (740 ml) of isopropyl alcohol; adding the isopropyl alcohol to the benzocaine and the menthol; obtaining and weighing 100 gms (100 ml) of distilled water; adding the distilled water to the benzocaine, the menthol and the isopropyl alcohol; and sealing and shaking the flask at 200 revolutions per minute for 60 minutes at approximately 25 C.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

FIG. 1 is a block diagram showing a range of a safe and effective quantity for the major components of a liquid form of the alcohol-based topical numbing agent (topical homogenous anesthesia chemical composition), in accordance with a non-limiting exemplary embodiment of the present disclosure;

FIG. 2 is a block diagram showing a preferred safe and effective quantity of the major components of a liquid form of the alcohol-based topical numbing agent (topical homogenous anesthesia chemical composition), in accordance with a non-limiting exemplary embodiment of the present disclosure;

FIG. 3 is a block diagram showing a range of a safe and effective quantity of the major components of a cream (non-liquid) form of the alcohol-based topical numbing agent (topical homogenous anesthesia chemical composition), in accordance with a non-limiting exemplary embodiment of the present disclosure;

FIG. 4 is a flow chart showing the steps of a method of utilizing an alcohol-based topical numbing agent for providing an anesthetic effect on skin tissue, in accordance with a non-limiting exemplary embodiment of the present disclosure; and FIG. 5 is a flow chart showing the steps of a method of preparing one liter of an alcohol-based topical numbing agent for providing an anesthetic effect on skin tissue, in accordance with a non-limiting exemplary embodiment of the present disclosure.

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

As used herein, the terms "alcohol-based topical numbing agent," "alcohol-based homogenous anesthesia chemical composition" and variations thereof are interchangeable.

As used herein, "gms" means grams.

As used herein, "ml" means milliliter.

As used herein, "% (v)" means percentage concentration is volume percent. This measures the amount of solute and solution in milliliters. The mathematical equation is:

Volume percent=volume of solute (in ml)/100 ml of solution)×100

As used herein, "% (w/v)" means percentage concentration is weight/volume percent or mass/volume percent. This measures the amount of solute in grams but measures the amount of solution in milliliters. The mathematical equation is:

Weight/Volume percent=weight of solute (in gms)/ volume of solution (in ml)×100

As used herein, "C" means Celsius.

The non-limiting exemplary embodiment(s) is/are referred to generally in FIGS. 1-5 and is/are intended to provide an alcohol-based topical numbing agent (alcohol-based topical anesthesia chemical composition 10, 10') that can be applied to an epithelial surface via a cotton swab or other suitable applicator. It should be understood that the exemplary embodiment may be used to numb various skin types, and should not be limited to any particular skin type described herein. The liquid form of the alcohol-based topical numbing agent (alcohol-based topical anesthesia chemical composition is referred to by reference numeral 10 and the non-liquid form (e.g., cream, ointment, gel) is referred to by reference numeral 10'.

In a non-limiting exemplary embodiment, an alcohol-based, liquid chemical composition 10 may be applied to human and animal skin for the purpose of administering local anesthesia before performing a procedure that may cause pain or discomfort. Of course, the alcohol-based, liquid chemical composition 10 may be used in situations without a procedure. Examples of this will be skin surface injuries such a 1st degree burns, abrasions, scratches, insect bites, etc. The disclosure may be embodied as a ready-to-use swab soaked in the liquid anesthesia. Notably, the chemical composition 10 is an alcohol-based anesthesia that resides in a liquid form; not gel or spray. The swab applicator allows better control during application of the alcohol-based liquid anesthetic, which is different from conventional topical "skin-numbing" agents. The terms "anesthesia" and "anesthetic" are interchangeably used throughout the present disclosure.

The acronym "USP" means United States Pharmacopeia, which is the official pharmacopeia of the United States. Prescription and over-the-counter medicines and other health care products sold in the United States are required to follow the standards in the USP National Formulary. The acronym "CAS" means Chemical Abstracts Services. A CAS Registry Number, also referred to as CASRN or CAS Number, is an unique numerical identifier assigned by CAS to every chemical substance described in the open scientific literature, including organic and inorganic compounds, minerals, isotopes, alloys and nonstructurable materials. The Registry maintained by CAS is an authoritative collection of disclosed chemical substance information. The USP and CAS acronyms are employed throughout the present disclosure.

The present disclosure prefers the use of an alcohol, preferably a low carbon alcohol, because low carbon alcohols have a relatively low value of heat of vaporization which makes them able to evaporate quickly at room temperature. It is this characteristic that gives the user the "cooling" sensation realized during application. In order to feel the cooling sensation, the alcohol needs to be present in the composition at high concentrations described hereinbelow. Thus, the alcohol-based topical anesthesia chemical composition 10, 10' of the present disclosure combines the antiseptic effect of isopropyl alcohol with the anesthetic effect of benzocaine using menthol as a counter irritant to cause an amplified effect.

In a non-limiting exemplary embodiment, the alcohol-based topical anesthesia chemical composition 10, 10' is an external analgesic and antimicrobial over-the-counter (OTC) drug for the preparation and numbing of the skin prior to finger sticks or laser and cosmetic procedures, for example, and the temporary relief of minor aches and pain associated with these procedures. The alcohol-based topical anesthesia chemical composition 10, 10' can provide effective cutaneous anesthesia as early as 1 (one) minute after application to skin tissue and is intended for external use only. Again aches and pain not associated with procedures could be treated with alcohol-based topical anesthesia chemical composition 10, 10'.

Initially, three anesthetic ingredients were considered to provide the anesthetic property of the present alcohol-based topical anesthesia chemical composition 10, 10', namely, benzocaine, lidocaine and tetracaine. All these three ingredients are on the generally recognized as safe (GRAS) list of the American Food and Drug Administration. However, only one of these can be used in a single preparation based on the FDA regulation. Based on our preliminary experience, we decided to use benzocaine as our "anesthetic of choice". The reason for this was the ability of benzocaine to provide rapid topical anesthesia in available topical anesthetics up to a 20% (w/v) concentration (maximum allowable by the FDA). In our experience, effective anesthesia is achieved by benzocaine in solutions containing 14% (w/v) or higher. The alcohol-based topical anesthesia chemical composition 10, 10' contains 15% (w/v) benzocaine, based on effectiveness and solution stability.

The present disclosure further includes a method 11 of utilizing an alcohol-based topical numbing agent for providing an anesthetic effect on skin tissue. Such a method 11 includes the steps of: obtaining a topical homogenous chemical composition including a primary solvent including a safe and effective quantity of isopropyl alcohol, a secondary solvent including a safe and effective quantity of water, at least one anesthetic including a safe and effective quantity of benzocaine, and a safe and effective quantity of a skin analgesic including menthol; and applying the topical homogenous chemical composition to an epithelial tissue of a user.

In a non-limiting exemplary embodiment, one liter of an alcohol-based topical anesthesia chemical composition 10 may be prepared by the following method 12 steps:
 1. Weigh 150 gms of benzocaine USP CAS: 94-09-7;
 2. Weigh 10 gms of menthol USP CAS: 1490-04-6;
 3. Add both solids (benzocaine and menthol) to a 2 liter sealed flask;
 4. Weigh 567 gms (740 ml) >99% Isopropyl Alcohol (IPA) USP CAS: 67-63-0;
 5. Add the IPA to the solids (benzocaine and menthol) in step 3;
 6. Weigh 100 gms (100 ml) double distilled water;
 7. Add the measured water to the benzocaine, menthol and isopropyl alcohol in step 5;
 8. Seal the flask and shake the mixture (benzocaine, menthol, isopropyl alcohol and distilled water) at 200 rpm for 60 minutes at room temperature (e.g., approximately 25 C); and
 9. When the solids (benzocaine and menthol) dissolve you will have a clear one liter homogenous solution of the alcohol-based topical anesthesia chemical composition 10.

In a non-limiting exemplary embodiment, the final concentrations of the ingredients of the alcohol-based topical anesthesia chemical composition 10 are as follows:
 benzocaine 15% (w/v)
 menthol 1% (w/v)
 IPA 74% (v)
 Water 10% (v)

In a non-limiting exemplary embodiment, the alcohol-based topical anesthesia chemical composition 10 may be stored in a tightly sealed container at 25 C or a temperature range of 20 C to 40 C. Temperatures below 15 C may cause the benzocaine to precipitate.

In a non-limiting exemplary embodiment, the alcohol-based topical anesthesia chemical composition 10 is a homogeneous solution composed (by volume) of Isopropyl Alcohol 74% (v) which is the main solvent. The other solvent is water 10% (v); inactive ingredient. There is preferably one anesthetic in the alcohol-based topical anesthesia chemical composition 10, namely (by weight volume), benzocaine 15% (w/v). The alcohol-based topical anesthesia chemical composition 10 also has a skin analgesic, menthol 1% (w/v). The unique characteristics of the alcohol-based topical anesthesia chemical composition 10 are: 1. It is an alcohol based topical liquid anesthetic, wherein conventional available skin anesthetics are cream based. 2. It is a topical anesthetic as well as an antiseptic solution due to its 74% (v) Isopropyl Alcohol content (qualifying solutions with greater than 60% (v) alcohol are antiseptics per FDA designation). 3. Due to its unique composition, it works fast, most cases within a minute of application compared to the cream based topical anesthetics that take up to 30 minutes to take effect. Such quantities of the above-mentioned ingredients are safe and effective in accordance with the true spirit and scope of the present disclosure.

In a non-limiting exemplary embodiment, alcohol-based topical anesthesia chemical composition 10 is provided in a liquid solution that may be packaged in varying configurations, including: varying sizes of plastic bottles with a spray dispensing tip; and individually sealed foil packages of various sizes with or without presoaked swabs for skin application.

The alcohol-based topical anesthesia chemical composition 10, 10' will be available as an over-the-counter (OTC) product which is regulated by the Monograph Label. Products applying the Monograph Label are restricted to use GRAS listed ingredients at the concentration allowed by the FDA. The developed Monograph Label is registered with the FDA listing the ingredients and their purpose in the product as "Drug Facts."

Isopropyl Alcohol is the most commonly used antiseptic alcohol in medical practice. Ethyl alcohol may also be used, however, due to abuse potential its use is further regulated. Concentrations of alcohol higher than 60% (v) are considered to provide adequate antiseptic property. The alcohol-based topical anesthesia chemical composition 10 solution has 74% (v) Isopropyl Alcohol.

The property of menthol as a counter irritant and analgesia combines both an effect on the local nerves and blood flow of the area where it is applied. When combined with benzocaine, there is a synergistic effect to provide rapid anesthesia. Menthol is a GRAS listed chemical. Higher concentrations of menthol have a slight risk of causing a chemical burn to the applied skin. With our preliminary work, we discovered, 1% (w/v) menthol provided a safe yet effective counterirritant analgesic property. Therefore, the alcohol-based topical anesthesia chemical composition 10 has 1% (w/v) menthol. Alternatives to menthol are not impressive. For example, Aloe Vera extract is a skin moisturizing agent and does not provide any analgesia. Hydrocortisone is an anti-inflammatory chemical and also does not provide immediate analgesia.

The alcohol-based topical anesthesia chemical composition 10, 10' provides the most effective use of the three GRAS listed ingredients to allow one solution to have both antiseptic and anesthetic properties. Other combinations could replace the benzocaine with lidocaine up to 4% (w/v) (maximum allowable) and tetracaine up to 3% (w/v) (maximum allowable). However, using benzocaine provides a wider range of allowable concentrations depending on the application of the product.

In non-limiting exemplary embodiments, the alcohol-based topical anesthesia chemical composition 10, 10' may include the following safe and effective quantity of ingredients:

TABLE 1

| | Isopropyl Alcohol | Benzocaine | Menthol | Water |
|---|---|---|---|---|
| Liquid Embodiment | 70-75% (v) | 5-20% (w/v) | 1-3% (w/v) | 2-24% (v) |
| Cream, Lotion and Ointment Embodiments | 5-15% (v) | 2-20% (w/v) | 0.1-1% (w/v) | 64-92.9% (v) |

With reference to Table 1 hereinabove, a broad range of the safe and effective quantities of various active ingredients for the liquid embodiment may be as follows: Isopropyl Alcohol 70% to 75% (v), benzocaine can range from 5% to 20% (w/v) with a most effective range from 14% to 20% (w/v). However, beyond 16% (w/v) of benzocaine, the solution stability becomes an issue due to the precipitation of benzocaine; and menthol can be effectively utilized in the range 1% to 3% (w/v).

With further reference to Table 1 hereinabove, a broad range of the safe and effective quantities of various active ingredients for the cream, lotion and ointment embodiments 10' may be as follows: Isopropyl Alcohol 5% to 15% (v) IPA; benzocaine can be lowered between 2% to 20% (w/v) due to added skin penetration enhancers in these embodiments; and menthol can be effectively utilized in the lower concentration of 0.1% to 1% (w/v).

Using the alcohol-based topical anesthesia chemical composition 10, 10', modifications of this solution can be incorporated in other products. For example, a scent free after shave balm will combine, benzocaine, IPA, Aloe Vera extract and a cream base. A product combining a percentage of the alcohol-based topical anesthesia chemical composition 10, 10' with 1% (w/v) hydrocortisone (maximum allowable) in an ointment or cream can be used as an Insect bite and Allergy soothing cream or as a Hemorrhoid relief ointment. Bandage impregnated with alcohol-based topical anesthesia chemical composition 10, 10' and topical antibiotic gel will be another application. A lotion spray incorporating the alcohol-based topical anesthesia chemical composition 10, 10' may be used for minor burns or as a sunburn relief lotion.

In a non-limiting exemplary embodiment, one or more penetration enhancers may be employed as an agent used to increase the permeability of the skin to a pharmacologically active agent to increase the rate at which the drug diffuses through the skin and enters the tissues and bloodstream. A chemical skin penetration enhancer increases skin permeability by reversibly damaging or by altering the physiochemical nature of the stratum corneum to reduce its diffusional resistance. In a review of the technical and patent literature, more than 275 different chemical compounds were found to be cited as skin penetration enhancers. Most of the compounds are generally recognized as safe (GRAS) ingredients that would often be considered inert by a formulator. Osborne D W, Henke J J, *Pharmaceutical Technology*, November 1997, pp 58-86. Examples of penetration enhancers include: alcohols, such as methanol, ethanol, although it is conceivable that denatured ethyl alcohol may be used alternatively, isopropyl alcohol; polyols, such as n-alkanols, limonene, terpenes, dioxolane, propylene glycol, ethylene glycol, other glycols, and glycerol; sulfoxides, such as dimethylsulfoxide (DMSO), dimethylformamide, methyl dodecyl sulfoxide, dimethylacetamide; esters, such as isopropyl myristate/palmitate, ethyl acetate, butyl acetate, methyl proprionate, and capric/caprylic triglycerides; ketones; amides, such as acetamides; oleates, such as triolein; various surfactants, such as sodium lauryl sulfate; various alkanoic acids, such as caprylic acid; lactam compounds, such as azone; alkanols, such as oleyl alcohol; dialkylamino acetates, and admixtures thereof.

In a non-limiting exemplary embodiment, the selection of the penetration enhancer is made depending on, for example, the solubility of each component, which may be included in the formulation. Two major classes of topical anesthetics used in the nonprescription treatment of pain are esters and amides. Examples of those in the ester class include benzocaine, butamben picrate and tetracaine. Examples of those in the amide class are dibucaine, prilocaine, etidocaine, mepivacaine, bupivicaine and lidocaine. Other examples are proprionic acid derivatives, fenamates, pyrrolealkanoic acids, pyrazolone derivatives, oxicams, pramoxine, and others and mixtures thereof.

The present disclosure is the only formulation that has menthol and the isopropyl alcohol, in addition to such penetration enhancers, which makes it unique and fast acting.

In a non-limiting exemplary embodiment, low carbon alcohols have a relatively low value of heat of vaporization, which makes them able to evaporate quickly at room temperature. It is this characteristic that gives the user the "cooling" sensation realized during application. In order to feel the cool sensation, it is necessary that the alcohol be present in the composition at high concentrations.

In a non-limiting exemplary embodiment, the present formulation and method are particularly useful in preparing for ablation, and prior to laser procedures requiring vaporization, excision, incision, and coagulation of soft tissue in medical specialties including dermatology, plastic surgery, podiatry, neurosurgery, gynecology, otorhinolaryngology (ENT), arthroscopy (knee surgery), and invasive and endoscopic general surgery.

In a non-limiting exemplary embodiment, the present method may be used for minor surgery procedures, such as cosmetic applications, which include, but are not limited to, laser resurfacing, electrolysis, permanent makeup application, body piercing, and tattooing.

In a non-limiting exemplary embodiment, the method of the present disclosure can be used on preemptive anesthesia and in post-operatory pain relief therapy, especially in pediatrics and overly emotional patients. The present disclosure relates to improved formulations and methods for the skin delivery of anesthetics to human and animal tissue and systems. The disclosure provides penetrating topical formulations and therapies, and is based on the use of a pharmaceutically-active agent dissolved in, or admixed with, a volatile penetration-enhancing carrier.

In a non-limiting exemplary embodiment, the chemical composition 10, 10' of this disclosure includes a safe and effective amount of an anesthetic, together with a volatile penetration-enhancing carrier that when contacted with patient skin, allows the volatile carrier to evaporate leaving the skin with a cool sensation, anesthetized and with more concentrated anesthetic present on the skin.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. §1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. An alcohol-based topical numbing agent for providing an anesthetic effect on skin tissue, said alcohol-based topical numbing agent comprising: a topical homogenous chemical composition including
   a primary solvent including a safe and effective quantity of isopropyl alcohol;
   a secondary solvent including a safe and effective quantity of water;
   at least one anesthetic including a safe and effective quantity of benzocaine; and
   a safe and effective quantity of a skin analgesic including menthol.

2. The alcohol-based topical numbing agent of claim 1, wherein said topical homogenous chemical composition is a liquid.

3. The alcohol-based topical numbing agent of claim 2, wherein said safe and effective quantity of isopropyl alcohol is between 70% (v) to 75% (v) of said topical homogenous chemical composition.

4. The alcohol-based topical numbing agent of claim 2, wherein said safe and effective quantity of benzocaine is between 5% (w/v) and 20% (w/v) of said topical homogenous chemical composition.

5. The alcohol-based topical numbing agent of claim 2, wherein said safe and effective quantity of water is between 2% (v) and 24% (v) of said topical homogenous chemical composition.

6. The alcohol-based topical numbing agent of claim 2, wherein said menthol is between 1% (w/v) and 3% (w/v) of said topical homogenous chemical composition.

7. The alcohol-based topical numbing agent of claim 2, wherein said safe and effective quantity of isopropyl alcohol is 74% (v) of said topical homogenous chemical composition, wherein said safe and effective quantity of benzocaine is 15% (w/v) of said homogenous chemical solution, wherein said safe and effective quantity of water is 10% (v) of said topical homogenous chemical composition, and wherein said menthol is 1% (w/v) of said topical homogenous chemical composition.

8. The alcohol-based topical numbing agent of claim 1, wherein said topical homogenous chemical composition is a cream.

9. The alcohol-based topical numbing agent of claim 8, wherein said safe and effective quantity of isopropyl alcohol is between 5% (v) to 15% (v).

10. The alcohol-based topical numbing agent of claim 8, wherein said safe and effective quantity of benzocaine is between 2% (w/v) and 20% (w/v) of said topical homogenous chemical composition.

11. The alcohol-based topical numbing agent of claim 8, wherein said safe and effective quantity of water is between 64% (v) and 92.9% (v) of said topical homogenous chemical composition.

12. The alcohol-based topical numbing agent of claim 8, wherein said menthol is between 0.1% (w/v) and 1% (w/v) of said topical homogenous chemical composition.

\* \* \* \* \*